Figure 1:
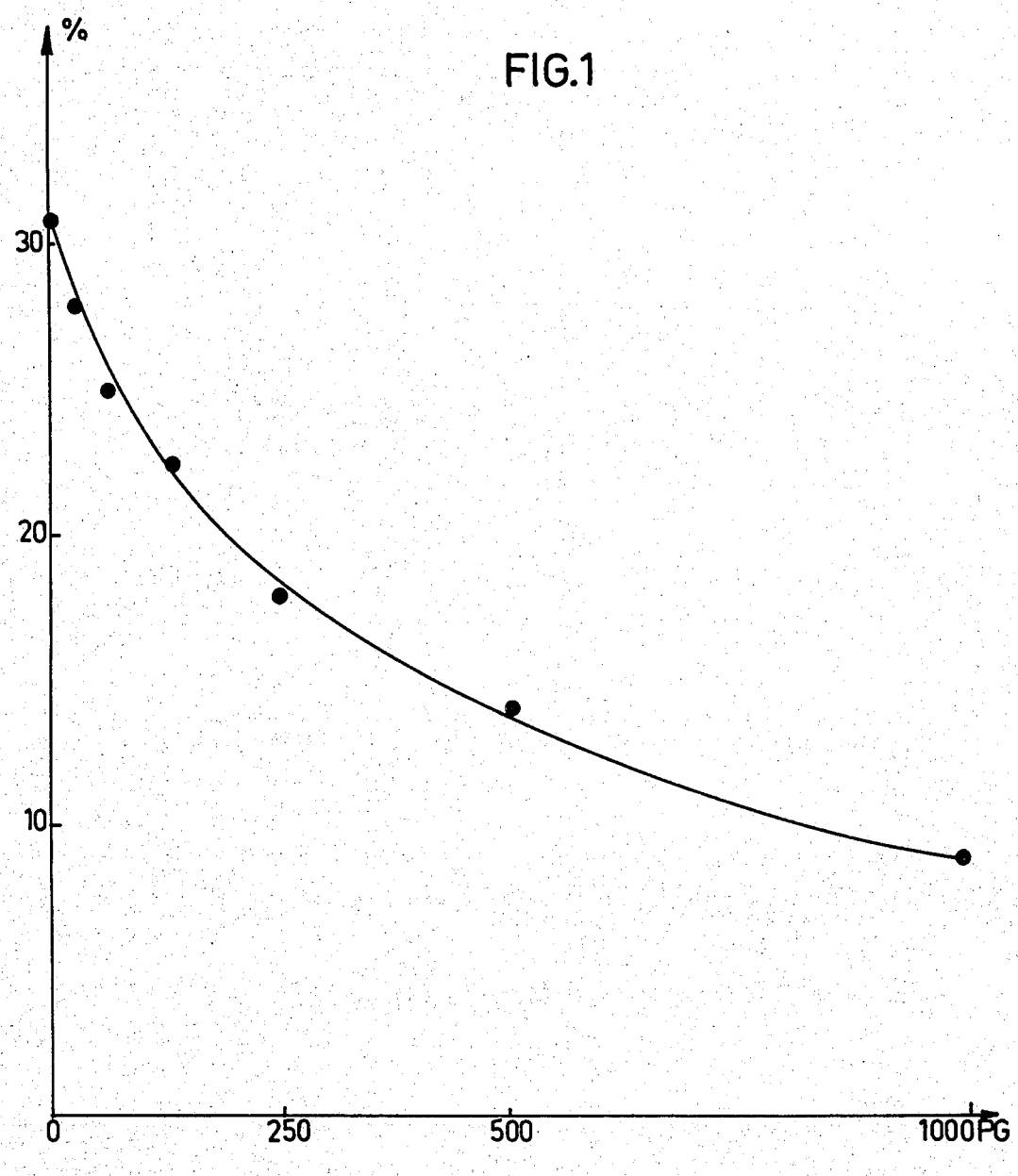

United States Patent [19]

Nicolas et al.

[11] 4,350,760
[45] Sep. 21, 1982

[54] METHOD FOR THE SEPARATION OF A PROTEIN SUBSTANCE FROM A SOLUTION CONTAINING THE SAME BY AFFINITY FILTRATION AND APPLICATION OF SAID METHOD TO ENZYMATIC ASSAYS

[75] Inventors: Jean-Claude Nicolas; Béatrice Térouanne; Bernard Descomps; André Crastes de Paulet, all of Montpellier, France

[73] Assignee: Institut National de la Sante et de la Recherche Medicale, Paris, France

[21] Appl. No.: 160,271

[22] Filed: Jun. 17, 1980

[30] Foreign Application Priority Data

Jun. 21, 1979 [FR] France .................................. 79 15992

[51] Int. Cl.³ ............................................ G01N 33/54
[52] U.S. Cl. ..................................... 435/7; 23/230 B; 210/635; 424/12; 435/26
[58] Field of Search .......................... 210/635, 198.2; 23/230 B, 230.3; 424/1, 1.5, 12; 435/7, 177, 188, 233, 26

[56] References Cited

U.S. PATENT DOCUMENTS

| | | | |
|---|---|---|---|
| 3,502,545 | 3/1970 | Westman et al. | 435/815 |
| 3,879,262 | 4/1975 | Schuurs et al. | 435/188 |
| 3,917,527 | 11/1975 | Shaltiel | 210/635 |
| 3,948,728 | 4/1976 | Röeschlau et al. | 435/223 |
| 4,125,492 | 11/1978 | Cuatrecasas et al. | 210/635 |
| 4,138,474 | 2/1979 | Updike | 210/635 |
| 4,205,130 | 5/1980 | Vihko | 210/635 |
| 4,235,960 | 11/1980 | Sasse et al. | 435/7 |
| 4,273,865 | 6/1981 | von Stetten et al. | 435/7 |

OTHER PUBLICATIONS

Baum et al. "Affinity Chromatography" Chapter 8, *Immobilized Enzymes Antigens, Antibodies, & Peptides*, Marcel Dekker Inc., N.Y., pp. 419-425.

*Primary Examiner*—Peter A. Hruskoci
*Attorney, Agent, or Firm*—Oblon, Fisher, Spivak, McClelland & Maier

[57] ABSTRACT

The invention relates to a method for the selective separation of a given protein substance having an affinity for a ligand from other substances some of them having the same affinity for the ligand but also having a high molecular weight, higher than that of said protein substance, said substances being in solution.

The method consists of filtering said substances on a gel which excludes said high molecular weight substances, said gel being coupled with a ligand for which said protein substance has affinity.

The method may be applied to enzymatic and especially to immunoenzymatic assays.

11 Claims, 3 Drawing Figures

METHOD FOR THE SEPARATION OF A PROTEIN SUBSTANCE FROM A SOLUTION CONTAINING THE SAME BY AFFINITY FILTRATION AND APPLICATION OF SAID METHOD TO ENZYMATIC ASSAYS

The present invention relates to the selective separation of protein substances from a solution containing the same, by affinity filtration; it also relates to the application of said method to enzymatic assays which use a binding agent and an enzyme-labelled substance, such as immunoenzymatic assays.

More particularly, the present invention relates to the selective separation of a given protein substance from other substances having a high molecular weight, higher than that of said given protein substance, said substances being in solution, for example in a biologic liquid.

Methods for the separation of protein substances, such as, for example, separation by filtration on a gel, or by chromatography, such as affinity chromatography, are already known. However, these methods, which are well known in the art, are attended by drawbacks. For example, filtration on a gel permits the user to obtain a filtrate containing the substances excluded by the gel, that is to say the substances having a molecular weight higher than a given value. This method is dependent on the nature and structure of the gel, for the gel will retain every substance having a molecular weight lower than the particular given value. Nevertheless, this method does not permit selective separation of a specific protein substance.

Another method for separating protein substances is gel chromatography. This method often requires the use of columns of gel having a substantial length with relatively long elution times, thus precluding rapid separation, which is often necessary in the biological field, e.g. in immunological assays. However, by affinity chromatography, which is frequently used for purifying enzymes or preparing antigen-enzyme conjugates (Exley D. and Abukneska, 1977, FEBS letters 79 pp. 301-304 and Lanner et al. (1977) Proceedings of an International Symposium, Vienna) it is not possible to separate two substances having the same affinity for the gel, but different molecular weights.

As examples of references relating to such previous separation methods the following may be cited:

U.S. Pat. No. 3,502,545 which relates to a process for separating water soluble polymer substances from unbound proteins or peptides by means of a semiporous gel.

This process uses a chromatography column containing a semi-porous gel having exclusion limits higher than the molecular weight of the water-soluble polymer substance and higher than the molecular weight of the water soluble unbound protein or peptide.

FR Patent application No. 78 03 388 (published under No. 2 379 552) relates to an activated matrix and an activation method for affinity chromatography. The activation consists of carbonylation of a polysaccharide with a suitable carbonylation agent. This reference relates only to substrates for affinity chromatography suitable for separation processes using affinity chromatography.

FR Pat. No. 70 45 844 (published under No. 2 074 027) relates to a process for coupling polymers with biologically active molecules. This process consists of coupling, by means of covalent bridges, at least two substances, at least one of which is a polymer, each substance containing at least one of the following functional groups: isonitrile, aldehyde or ketone, anion primary or secondary amine; the coupling reaction is carried out in a reaction mixture containing the specific substances with possible supplemental substances, so that all functional groups are simultaneously present at the beginning of the reaction. The coupled products obtained by this process are suitable for affinity chromatography substrates.

FR Pat. No. 73 16 880 (published under No. 2.184.054) relates to a process for separating biologically active compounds by affinity chromatography on selective adsorbents.

Now, there has been found a method for the selective separation of at least one protein substance having an affinity for a ligand, from other substances, some of them having the same affinity for said ligand but also having a high molecular weight, higher than that of said protein substance, said substances being in solution, said method consisting in filtering the solution containing said substances on a gel excluding said substances of high molecular weight, said gel being coupled with a ligand for which said protein substance has affinity.

Therefore, the invention method allows selective separation of at least one protein substance having an affinity for a ligand from substances, some of them having affinity for the same ligand but also having a high molecular weight, higher than the one of said protein substance. As a matter of fact, due to the choice of the gel, the high molecular weight substances, higher than the one of the protein substance, will be excluded, whether or not said substances have an affinity for the ligand. The other substances present in the solution and able to penetrate into internal network of the gel due to their molecular weight will not be selectively retain on the gel, in as much as they are free from affinity for the ligand.

The recovering of said protein substances, after affinity filtration, may be made, after washing of the gel, by elution according to suitable means known by one skilled in the art, such as with pH modification or by competition with an excess of ligand in solution.

It should be noted that in the preferred use of the invention method, i.e. in enzymatic assays, the recovering of the protein substances is not required since the enzymatic activity measurement is effected on the filtrate as will be explained hereinafter.

The gel used in the method according to the present invention should be a cross-linked gel, so that it excludes the substances having a high molecular weight, higher than that of the protein substance to be separated. In other words, the gel used in the method of the invention should have a pore-size such as to ensure exclusion by the gel of the substances having a high molecular weight, higher than that of said considered protein substance.

By way of examples of gels suitable for the purpose of the invention, there may be mentioned gels of polyacrylamide, of agarose, of polyacrylamide-agarose, of dextran, of polysaccharides and the like, especially those gels known under the trade names of Ultrogel, Sephadex, Biorad, Sepharose etc.

The gel used according to the method of the invention is coupled with a ligand for which the protein substance to be separated has affinity. The gel-ligand coupling is effected according to known processes, for instance by activating the gel with glutaraldehyde, cyanogen bromide, or bis epoxides, and coupling with the ligand by methods within the knowledge of those skilled in the art. In this connection, reference may be made to Methods in Enzymology-Vol. 34, pages 13-102.

The amount of ligand coupled with the gel is dependent on the affinity of the particular protein substance for the ligand. An amount of about 25-200 times, e.g. 50 times, the association coefficient of the protein substance with respect to the ligand was found to be suitable for the purpose of the invention.

In the meaning of the present invention, the expression "protein substance" designates proteins themselves, such as well as enzymes, antibodies, antigens and the like, as protein-bearing conjugates, for example, enzyme labelled substances used in enzymatic assays.

The method according to the present invention finds a particularly valuable application in the field of enzymatic assays that use a binding agent and an enzyme-labelled substance. By way of examples of such enzymatic assays, immunoenzymatic assays may be especially mentioned.

The important developments effected in enzymology made it possible to replace radioimmunological assays by immunoenzymatic assays using an enzyme as a labelling agent, instead of the radioactive labelling agents used heretofore. Numerous bibliographic references are available in the field of immunoenzymatic assays. Reference may be made, for instance, to the article by S. Avrameas "Détection d'anti-corps et d'antigènes à l'aide d'enzymes" (antibody and antigen detection by means of enzymes) Bull. Soc. Chim. Biol.1968,50, Nos 5-6.

It will be recalled that enzymatic assays, such as immunoenzymatic assays, fall within two classes, viz. direct assays on the one hand and competitive assays on the other hand. Besides, various means are available for separating the unreacted enzyme-labelled substance from the complexes formed in the assaying process. An example of such means consists of using one of the assaying reagents in an insolublized form. In this connection, mention may be made in particular of the well known technique of assay with an immunoadsorbent. A particular immunochemical compound suitable as immunoadsorbent is disclosed in DE-OS Patent application No. 2 719 772.

Another means, which is also well known in the immunoenzymatic field is the technique of so called double antibody assay, consisting of causing precipitation of the complex formed during assaying by means of an antibody of said complex. Processes requiring the use of an immunoadsorbent are called "heterogeneous". These processes involve on the one hand the preparation of such an immunoadsorbent, which can be used but once, and on the other hand a number of washing and centrifuging steps to separate the immunoadsorbent from the reaction medium. As a matter of fact, it is preferable to determine the enzymatic activity of the fraction bound to the immunoadsorbent so as to ensure more precise determination. Therefore, automation of such enzymatic assaying processes is difficult.

Some examples will be given hereafter of immunoenzymatic assays, using immunoadsorbents to assays for antigens. In this connection, the term antibody "(antigen) enzyme conjugate" will be used to designate the enzyme-labelled antibody or antigen and the term "free (or unbound) antibody (antigen)-enzyme conjugate" to designate the antibody (antigen)-enzyme conjugate having not reacted during the immunoenzymatic assay.

A well known process for immunoenzymatic assay of an antigen consists of:
incubating the antigen to be assayed together with an antibody-enzyme conjugate,
adding to the resulting reaction medium on insolubilized antigen, e.g. an antigen bound to an immunoadsorbent which will react with the free antibody-enzyme conjugate,
separating the solid phase from the liquid phase and measuring the enzymatic activity of one of said phases.

A process for competitive immunoenzymatic assay of antigens consists of:
incubating the antigens to be tested together with an antigen-enzyme conjugate and an antibody, thus using the competition between the antigen to be assayed and the antigen-enzyme conjugate with respect to the antibody, the latter being under an insoluble form, for example bound to an immunoadsorbent,
separating the liquid phase which contains the free antigen-enzyme conjugate from the solid phase comprised of the antigen-enzyme/antibody complex, and
measuring the enzymatic activity of one of the two phases.

Another process of immunoenzymatic assay for antigen determination is the double antibody assay consisting of:
incubating the antigen to be assayed together with a determined quantity of an antigen-enzyme conjugate and an antibody $Ac_1$,
then incubating the resulting reactive mixture together with a antibody $Ac_2$ which is the antibody of the antigen-enzyme complex formed in the first step, said antibody $Ac_2$ being bound to an immunoadsorbent,
separating the liquid phase from the solid phase, and measuring the enzymatic activity of one of the two phases.

The above-described assay methods, which may also be used for antibody determination, are given by way of illustration of methods involving the use of an immunoadsorbent.

These examples show that a solid phase/liquid phase separation is always necessary, said separation requiring washing and centrifuging steps which prevent automation of said immunoenzymatic assay methods. Moreover, as indicated above, the immunoadsorbent can be used but once, this requiring the use of substantial amounts of insoluble/substrate/antigen (antibody) coupling reactions for producing the appropriate immunoadsorbent.

The separation method according to the present invention may be advantageously applied to the enzymatic assay processes, wherein a binding agent and an enzyme-labelled substance are used, to separate the unreacted enzyme-labelled substance from the complexes formed during the assay. The term "complexes formed during the assay" designates the reaction product or products of at least one binding agent with an enzyme-labelled substance, which are formed during the enzymatic assay according to the selected type of assay, e.g. direct assay, competitive assay, sandwich assay, double antibody assay and the like.

The separation method according to the invention avoids the use of immunoadsorbent and thus the above-mentioned washing and centrifuging steps. Thus, enzymatic assays, such as immunoenzymatic assays, are effected more rapidly and can be automated, this being of considerable practical interest.

Therefore, according to another feature, the present invention relates to a method for either direct or competitive enzymatic assay of the reaction products of at least one binding agent with an enzyme-labelled substance, said binding agent having affinity for said enzyme-labelled substance, consisting of reacting said binding agent to be assayed with said enzyme-labelled substance in case of a direct assay, or said binding agent with said enzyme-labelled substance and said substance to be assayed in the case of a competitive assay, said process comprising the steps of separating said unreacted enzyme-labelled substance from said reaction product or products by affinity filtration of the solution obtained after reaction on a gel coupled with a ligand for which the enzyme has affinity, said gel having pores of a size sufficient to exclude said reaction product or products having a high molecular weight higher than that of the enzyme-labelled substance, and measuring, in known manner, the enzymatic activity of the thus filtered solution.

Examples of binding agents which can be used according to the invention are binding proteins, such as antibodies, transport proteins, e.g. transcortin, hormonal receptors and the like. Products which can also be considered as binding agents are polyfunctional antigens or high molecular weight antigens; in this case, the ligand for the antigen will be the specific antibody examples of such antigens are polypeptides, polysaccharides, polynucleotides and the like.

The enzyme-labelled substance may be any substance having affinity for the binding agent, i.e. that may be considered as the ligand of the binding agent.

The binding agent will be either the assay reagent in the case of a competitive assay, or the substance to be assayed in the case of a direct assay.

By way of illustration, table I shows various examples of enzymatic assays which may be effected by the method according to the invention.

The gel used in the enzymatic assay method according to the invention is such as defined above and may be selected from the group consisting of gels of polyacrylamide, agarose, polyacrylamide-agarose, polysaccharides, dextran etc., provided that it has pores of sufficient size to exclude said reaction product or products having a molecular weight higher than that of the enzyme-labelled substance. Moreover, the gel must be coupled with a ligand for which the enzyme has affinity. Such ligands are selected from, among other, enzyme-inhibitors, co-enzymes and enzyme-substrate materials. Those skilled in that art will readily determine the ligand to be used as a function of the enzyme used, and select the suitable way of coupling is a function of the selected ligand and gel. However, reference may be made with advantage to the article "Methods in Enzymology", vol. 34, pp. 13–102, wherein the principal ways of coupling are described.

By way of examples, it will be mentioned that, when the enzyme is a dehydrogenase with NAD(P)i.e. an enzyme with NAD or NADP pyridin nucleotides), use may be made, as the ligand of the NAD (nicotinamide-adenin-dinucleotide) and of the NADP (nicotinamide-adenin-dinucleotide-phosphate), the AMP (adenosin monophosphoric acid) or the ADP (adenosin diphosphoric acid), which are co-enzymes of the dehydrogenase.

The dehydrogenase suitable for use in the method of the invention are dehydrogenase with high specific activity, such for example as glutathion reductase, glucose 6 phosphate dehydrogenase, malate-dehydrogenase, dehydrogenase alcohol.

When the enzyme is the $\Delta 5,3$-keto-steroid isomerase, then the ligand used may be an oestradiol derivate, the oestradiol being an inhibitor of this enzyme, such for example the oestradiol coupled at $17\beta$ with glutathion. In the latter case, the gel-ligand coupling may be effected by activating the gel with cyanogen bromide, glutaraldehyde or any other coupling agent well known in the art.

Thus, the gel used according to the invention constitutes a separating means suitable for enzymatic assays which permits, by mere affinity, filtration, to retain only the unreacted enzyme-labelled substance and to obtain a filtrate containing the reaction product or products, the enzymatic activity of which will be measured in known manner. Consequently, the enzymatic assay methods according to the invention can be easily automated, either on continuous flow type or on centrifugal type apparatus. Said automatization is made possible due to the rapid binding between the gel coupled with a ligand and the unreacted enzyme-labelled substance and to the possible repeated use, since mere washing of the gel is sufficient to remove the enzyme-labelled substance bound by affinity to said gel.

The enzymatic assay method according to the invention is especially suitable for assays of antigens and antibodies. Thus, for example, it is easy to effect according to the invention the assay of an antigen, the enzyme-labelled substance being on antibody-enzyme conjugate, the antibody being specific to the antigen; there will be obtained, after incubating the biological liquid containing the antigen to be assayed, together with the antibody-enzyme conjugate a solution containing, on the one hand, the unbound or free antibody-enzyme conjugate and, on the other hand, the antigen/antibody-enzyme complex. The gel used according to the invention should be such as to exclude the antigen-antibody-enzyme-complex and not the antibody-enzyme conjugate, and should include a ligand for which the enzyme has affinity; then, only the unbound antibody-enzyme conjugate will be retained by the gel.

According to an another embodiment, the method of the invention may be applied to competitive assays of antigens. Then, use should be made of an antigen-enzyme conjugate as an enzyme-labelled substance and of an antibody specific to the antigen to be assayed, said specific antibody forming the binding agent. Incubation of the biological liquid containing the antigen under assay together with the antigen-enzyme conjugate and the specific antibody leads to formation of a solution containing the unbound antigen-enzyme conjugate, an antibody/antigen complex to be assayed and an antibody/antigen-enzyme complex. The gel used in this process to separate the unbound antigen-enzyme conjugate from the complexes should have a pore size such that it will exclude those complexes which have a molecular weight relatively high with respect to the unbound antigen-enzyme conjugate, and will retain selectively said conjugate due to the presence of a ligand for which the enzyme has affinity.

Labelling of the substance by an enzyme is effected by methods well known in the art. In this connection, reference may be had to the article "Methods in Enzymology", vol. 25, part B, pp. 623–651.

There will be given hereafter typical examples of immunoenzymatic assays according to the invention using Δ5,3-keto-steroid isomerase as an enzyme, the ligand coupled to the gel being oestradiol-glutathion. In this particular case, the method of immunoenzymatic assay according to the invention may be used with advantage for assaying antigens consisting either of substances of the peptide type, such as protein substances, for example alphafoetoprotein, peptidic hormones, e.g. the human placental lactogen hormone PLH or of substances of the steroid type such as steroidal hormones, e.g. progesterone.

Thus, a preferred embodiment of the method of the invention comprises a method for immunoenzymatic assay of antigens of the peptide- or steroid-type contained in a biological liquid, comprising the steps of incubating said antigens to be assayed with an antigen-Δ5,3 keto-steroid isomerase conjugate and antibodies specific of said antigens, using as the assay reagent the progesterone- Δ5,3-keto-steroid isomerase conjugate or the human placental lactogen hormone- Δ5,3 keto-steroid isomerase conjugate.

The application of Δ5,3-keto-steroid isomerase in immunoenzymatic assays is described in details in French patent application No. 78 22 867 in the name of the assignee, as well as the ways of obtaining the antigen- Δ5,3-keto-steroid isomerase conjugates.

However, it will be recalled that, when the antigen is of peptidic nature, the antigen- Δ5,3-keto-steroid isomerase conjugate is produced through disulphide-bridge coupling by reacting on the one hand the peptide type substance and for example methyl 4-mercaptobutyrimidate and on the other hand, Δ5,3-keto-steroid isomerase and for example S-acetylmercaptosuccinic anhydride, and by coupling the respective reaction products, this leading to a conjugate wherein one mole of enzyme is coupled to one mole of peptide substance and which still retains at least 50% of its enzymatic activity after purification, the latter being effected in known matter by affinity chromatography.

When the antigen is of a steroidal nature, then the antigen- Δ5,3-keto steroid isomerase conjugate is obtained through coupling by means of a thiol residue by reacting, on the one hand, the steroidic substance with for example bromoacetic acid having the formula Br—CH$_2$—COOH, in the presence of carbodiimide, and on the other hand, Δ5,3-keto-steroid-isomerase with for example S-acetyl-mercaptosuccinic anhydride, and by coupling the respective reaction products.

In this particular case, use may be made of gels excluding substances of a molecular weight higher than about 100,000. Examples of suitable gels are those polyacrylamideagaroze gels known under the trade name "Ultrogel", such as Ultrogel AcA 34 and AcA 44, marketed by IBF (Industrie Biologique Française).

The method of the invention is also suitable for direct assay of antigens, such as alphafoetoprotein.

In this case, it is necessary to form antibody-enzme conjugate by suitable means, for example by coupling with disulphide bridges. Such a coupling may be carried out by reaction of the antibody on one hand and the enzyme on the other hand, with S-acetylmercapto succinic anhydride and by coupling of the resulting products. In this manner a conjugate of anti-alphafoetoprotein antibody and Δ5,3-keto-steroid-isomerase was prepared.

According to an another embodiment of the method of the invention, there may be used moreover an antibody of the binding agent so as to increase the molecular weight of said binding agent and thus bring forth a greater difference in molecular weight between the unreacted enzyme-labelled substance and the reaction products formed in the assay process.

The invention will now be illustrated by examples of immunoenzymatic assays using Δ5,3-keto-steroid-isomerase as an enzyme for competitive assay, on the one hand of progesterone and on the other hand of human placental lactogenic hormone PLH and for direct assay of alphafoetoprotein.

It should however be understood that these examples imply no limitation of the scope of the invention, and that the method of immunoenzymatic assay of the invention may be used for any assay requiring separation of the unbound protein substance-enzyme conjugate from the complexes formed in the assay.

EXAMPLE (1) Preparation of the antigen-enzyme conjugates

The procedure used was that described in French patent application No. 78 22 867.

Δ5,3-keto-steroid-isomerase was thiolated with S-acetyl-mercaptosuccinic anhydride, pH 7; after dialysis and hydrolysis of the S-acetyl group with hydroxylamine 0.1 M, pH 8; the enzyme was then dialyzed.

(a) Progesterone- Δ5,3-keto-steroid isomerase conjugate

A progesterone derivate, viz. 11α -bromoacetoxy-progesterone, was prepared separately by esterification of 11α -hydroxyprogesterone with bromoacetic acid in the presence of dicyclohexyl-carbodiimide. The reaction product was purified by silica gel chromatography.

Then 10 mg of 11α -bromoacetoxy-progesterone were reacted with 0.5 mg of thiolated enzyme (6 thiol groups per mole of enzyme) prepared by the above procedure. The reaction proceeded during 16 hours at pH 8.2 and at ambient temperature. After reaction, the steroid in excess was removed by filtration on a "Sephadex G 25" gel. Two moles of steroid reacted with 1 mole of enzyme.

According to the same procedure as cortisol- 66 5,3-keto-steroid isomerase conjugate was obtained.

b-PLH- Δ5,3-keto-steroid isomerase conjugate

Δ5,3-keto-steroid isomerase was thiolated according to the above-described procedure.

The PLH derivate was prepared by a disulphide bridge exchange reaction by reacting PLH with methyl 4-mercaptobutyrimidate as follows:

2 mg of PLH were dissolved in 300 μl of water brought to pH 9.5 with 100 μl of carbonate-bicarbonate buffer 0.1 M and were added with 1.3 mg of methyl 4-mercaptobutyrimidate.

Then the PLH derivate prepared as above was reacted with the thiolated enzyme activated by dithio nitrobenzoate; after a 16 hour reaction time, the excess of PLH was removed by affinity chromatography.

(c) Conjugate of anti-alphafoetoprotein and of Δ5,3-keto-steroid-isomerase.

Anti-alphafoetoprotein antibodies (IgG) were reacted with S-acetylmercapto-succinic anhydride by using the operating method hereinabove disclosed for Δ5,3-keto-steroid isomerase The S-acetyl groups were hydrolysed with hydroxylamine 0.1 M pH 8.

The IgG enriched with thiol groups were incubated within a night with Δ5,3-keto-steroid-isomerase, thiolated according to the above mentioned procedure and activated with dithio-nitrobenzoate. The IgG excess was eliminated by chromatography on Sepharose 4 B glutathion-oestradiol.

(2) Coupling of the gel with oestradiol 17β glutathion (a) Preparation of the oestradiol 17β glutathion derivative Oestradiol 17β -bromoacetate was prepared by estrification of oestradiol (300 mg) with bromoacetic acid (500 mg) in the presence of 700 mg of dicyclohexylcarbodiimide, the reaction medium being formed of 2 ml of dimethylformamide or tetrahydrofuran. After a 16 hour reaction time, the products were separated on a silica gel column.

60 g of oestradiol 17β-bromoacetate dissolved in 1 ml of dimethylformamide were incubated with 300 mg of reduced glutathion in 5 ml of tris buffer 0,1 M, pH 8.5, containing 50% of ethanol and 50% of dimethylformamide. After a 16 hour reaction time, 20 ml of water were added and the aqueous phase was twice extracted with 50 ml of ether. The aqueous phase was then deposited on a "Dowex" 1×2 (1.5×7 cm) column balanced at pH 7. After washing with 100 ml of citrate buffer 0.1 M, pH 6.5, then 100 ml of citrate buffer 0.1 M, pH 2, the column was eluated with 50 ml of citrate buffer 0.1 M, pH 2, containing 50% of ethanol. The pH of the eluate containing the oestradiolglutathion derivative was adjusted to pH 9.

(b) Gel-oestradiol derivate coupling

Polyacrylamide-agarose (Ultrogel Ac34 or Ultrogel Ac44) was coupled by reacting 100 ml of gel with 30 mg of the above prepared oestradiol derivate according to the following procedure: 100 ml of gel were activated with 10 g of cyanogen bromide at pH 11; after a 5 minute reaction time, the gel was washed with 1 liter of water and 200 ml of sodium bicarbonate buffer 0.1 M, pH 9. The gel was added to gluthathion oestradiol derivate in solution in 50 ml of sodium bicarbonate buffer 0.1 M pH 9 containing 50% of ethanol. After a 16 hour reaction time, the gel was washed with this same buffer, then with 1 liter of water. The oestradiol concentration in the gel phase was determined after hydrolysis by hydroxylamine M, pH 9, and enzymatic assay of the liberated oestradiol. The oestradiol concentration in the gel was 7,5 $10^{-5}$ M.

(3) Immunoenzymatic assay (a) Competitive assay

Competitive assay was effected by using antibodies specific to progesterone or to PLH and anti-γ globulin antibodies, the latter being utilized to increase the molecular weight of the specific antibody. The competitive reaction was carried out in polypropylene tubes.

100 μl of the antigen solution to be assayed were incubated with 100 μl of specific antibodies, 100 μl of anti-γ globulin antibodies and 100 μl of the antigen-enzyme solution (0,05 IU). After a 1 hour reaction time, 500 ml of buffer were added and the content of each tube was filtered on microcolumns (100 μl) of the Ultrogel-oestradiol gel prepared according to the above procedure. The number of microcolumns was equal to the number of tubes required for the assays. The enzymatic activity of the filtrate was determined by spectrophotometry at 248 nm. Thereafter, the gel was regenerated by washing with water.

It has been found that, with these conditions, 95% of the antibody/antigen-enzyme complex is recovered after filtration on the gel, while 98% of the unbound antiogen-enzyme conjugate is retained on the gel.

The above assay was repeated using different quantities of antigens to be assayed (PLH or progesterone).

Figure 2:
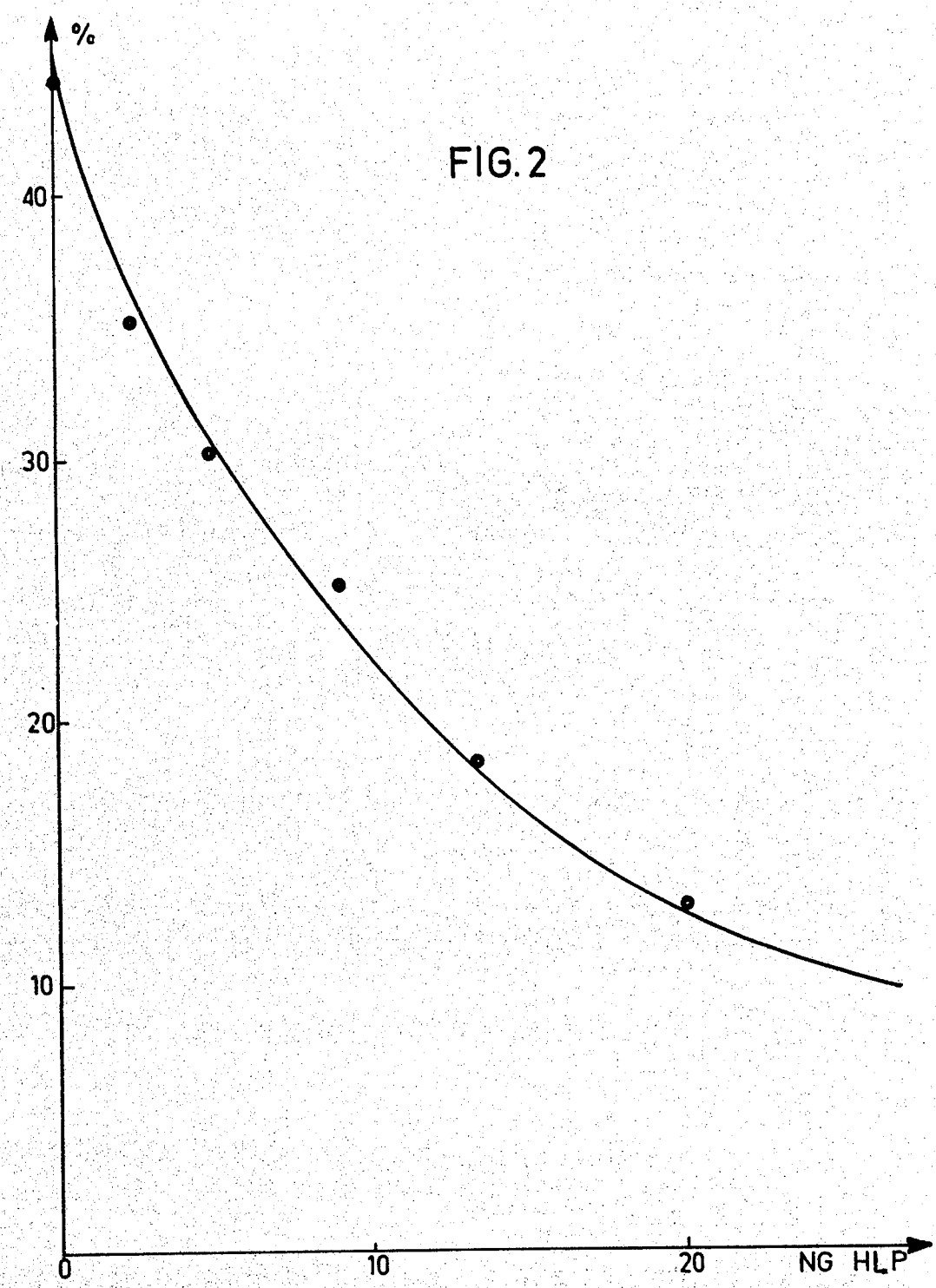

After filtration of the solution obtained after incubation on 0.1 ml of gel, the enzymatic activity of the solution or filtrate was measured. The results obtained are set forth in appended FIGS. 1 and 2, FIG. 1 relating to the progesterone and FIG. 2 to the human placental lactogenic hormone PLH; on said figures, the enzymatic activity in % is plotted in ordinates and the determined amount of antigen is plotted in abscissae. These results show that the enzymatic activity of the filtrate decreases as the amount of antigen increases.

This method of assay gives results similar to those of other assay methods (radio-immunological assays or immunoenzymatic assays using an immunoadsorbent). The present method is more rapid, since it requires but one filtration step and permits direct determination of the enzyme on 200 μl aliquots. A quantity of enzyme of 0.1 IU (international units) corresponds to 50 fentomoles of the antigen; usually 30–40% of the antigen-enzyme conjugate is bound by the specific antibodies in the absence of the unbound antigen (i.e. the antigen to be assayed). This enzymatic activity, determined on aliquots of 200 μl, will vary from about 200 to about 40 milliunits of absorbance per minute. This strong enzymatic activity affords good reproducibility and no interference with the serum was noted. In fact, only the serum at the final stage of gestation is capable of inhibiting the enzyme since the oestradiol concentration is very high and can inhibit the enzyme, but in practice the serums to be tested are sufficiently diluted to avoid any interference in the assay process.

(b) direct assay:assay of alphafoetoprotein

50 μl of the conjugate of anti-alphafoetoprotein and of Δ5,3-keto-steroid-isomerase prepared as above mentioned were incubated with increasing quantities of alphafoetoprotein (0.1 to 10 ng in 500 μl) After 2 hours of incubation at ambient temperature 500 μl of phosphate buffer 0.1 M were added to these solutions; these solutions were filtered on 100 μl of gel (Ultrogel AcA-34 -glutathionoestradiol). The IgG isomerase conjugate in excess was retained on the column (98%) whereas the complex alphafoetoprotein-IgG isomerase of higher molecular weight was excluded by the gel.

Figure 3:
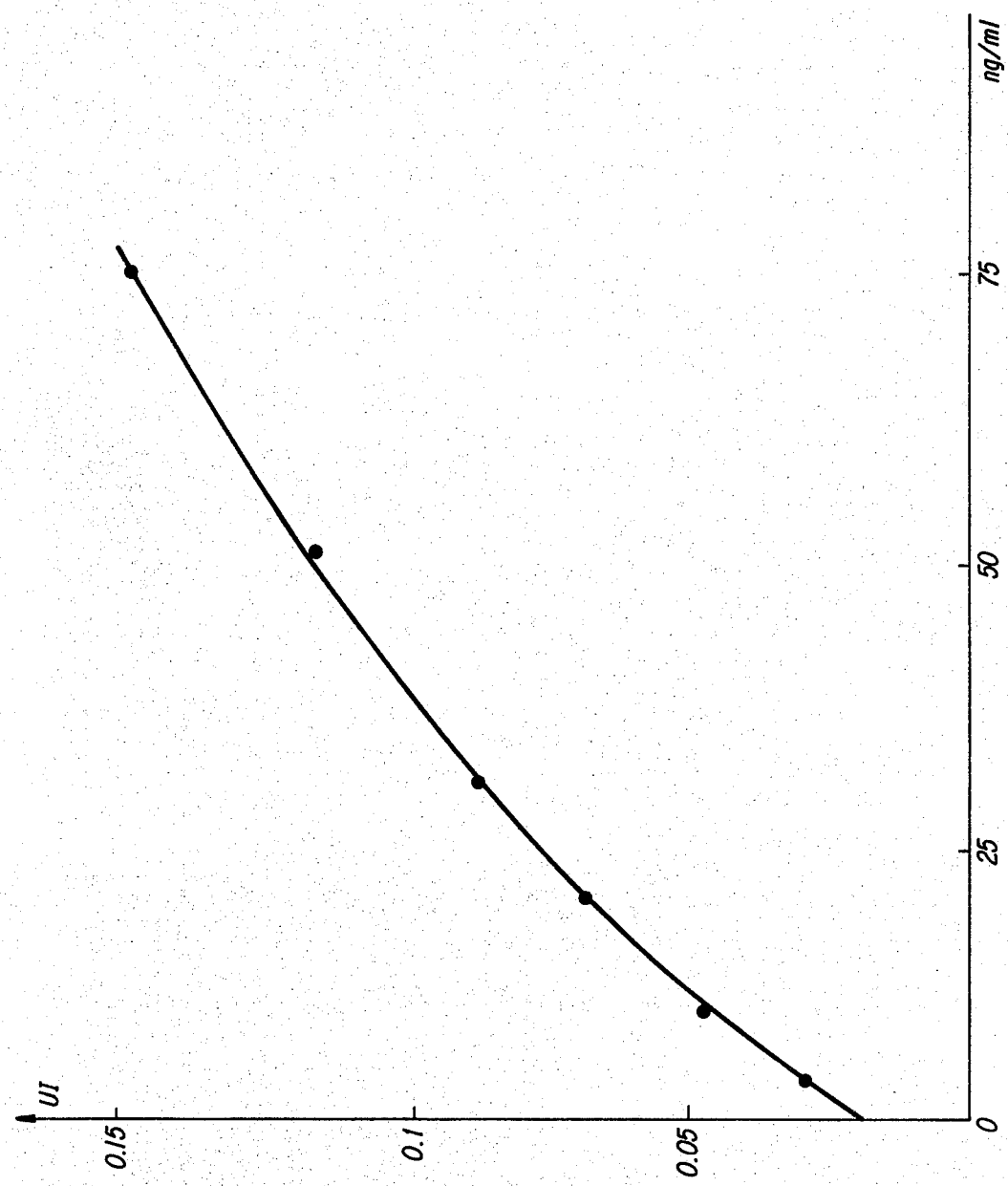

The enzymatic activity was proportional to the antigen quantity present in the incubation medium. The results obtained are represented on FIG. 3 on which were indicated on ordinate axis the enzymatic activity (IU) of the filtrate and on the abscissa axis the alphafoetoprotein quantity in the sample to be tested. The measured enzymatic activity is a function of the concentration of alphafoetoprotein in the sample to be tested.

TABLE I

| Substance to be assayed | Enzyme-labelled substance X*e | Binding agent | Reaction products | Type of assay |
|---|---|---|---|---|
|  | Ag*e | Ac? | Ag*e - Ac?; Ag*e | Direct assay of the antibody |
| Ag? | Ag*e | Ac | Ag*e - Ac; Ag*e Ag? - Ac | by competition of the antigen |
|  | H*e | R? | H*e - R?; H*e | Direct assay of the receptor |
| H? | H*e | R | H? - R; H*e H*e - R | Assay by competition of the hormone |
|  | L*e | P? | L*e - P?; L*e | Direct assay of the transport protein |
| L? | L*e | P | $L_{L}*e - P_{L}*e$ L? - P | Assay by competition of the ligand |
|  | Ac*e | Ag? | Ac*e - Ag?; Ac*e | Direct assay of antigen |
| Ac? | Ac*e | Ag | Ac*e - Ag; Ac*e Ac? - Ag | Assay by competition of antibody |

Legend
Ag = Antigen
Ac = antibody
H = Hormone
L = Ligand
R = Receptor
P = Transport protein
X*e = Enzyme-labelled substance (X = Ag, H, L, Ac . . .)
Ag? = Antigen to be assayed.
H?, L? and Ac? are respectively hormone, ligand or antibody to be assayed.

What we claim is:

1. A method for the direct enzymatic assay for the presence of a binding agent by assaying for the product of reaction of a binding agent with an enzyme labeled substance, said binding agent having affinity for said enzyme-labeled substance, comprising the steps of:
   reacting said binding agent with said enzyme-labeled substance to give a reaction solution containing a reaction product having a molecular weight higher than the molecular weight of said enzyme-labeled substance;
   separating enzyme-labeled substance from said reaction product by filtering said solution through a gel having pores of a size sufficient to exclude said reaction product, said gel being coupled with a ligand for which said enzyme has affinity; and
   measuring the enzymatic activity of said solution after said solution passes through said gel.

2. A method for the competitive enzymatic assay for the presence of a substance, comprising the steps of:
   contacting a first solution suspected of containing said substance with an enzyme-labeled substance, wherein said enzyme-labeled substance is said substance labeled with an enzyme, and a binding agent, wherein said binding agent has affinity for said substance and said enzyme-labeled substance, to give a second solution whereby said binding agent reacts with said substance present in said first solution to give a first reaction product and with said enzyme-labeled substance to give a second reaction product;
   separating said enzyme-labeled substance from said second reaction product by filtering said second solution through a gel having pores of a size sufficient to exclude said second reaction product, said gel being coupled with a ligand for which said enzyme has affinity; and
   measuring the enzymatic activity of said second solution after said second solution passes through said gel.

3. Method for enzymatic assay according to anyone of claim 1 or 2, wherein the binding agent is selected from the group consisting of antigens, antibodies, transport proteins, and hormonal receptors.

4. Method according to claim 1 or 2 nature, wherein an antigen-$\Delta 5,3$-keto-steroid isomerase is used as the enzyme-labelled substance, wherein the gel is coupled with oestradiol 17$\beta$ glutathion, and wherein said gel is selected from the group consisting of gels of polyacrylamide, agarose or polyacrylamide-agarose.

5. Method according to claim 4, wherein the antigen is progesterone or human placental lactogenic hormone.

6. Method according to claim 5, wherein the gel is coupled with oestradiol 17$\beta$ glutathion after activation of the gel by cyanogen bromide.

7. Method according to claim 6, wherein the quantity of is an antigen is being determined.

8. Method according to claim 7, wherein the antigen is alphafoetoprotein.

9. The method of claim 7, wherein the gel is coupled with oesteradiol 17$\beta$ glutathion after activation of the gel by cyanogen bromide.

10. The method of claim 9, wherein the quantity of an antigen is being determined.

11. The method of claim 10, wherein the antigen is alphafoetroprotein.

* * * * *